United States Patent [19]
Hsu et al.

[11] Patent Number: 5,380,734
[45] Date of Patent: Jan. 10, 1995

[54] N-CYANOAMIDINE DERIVATIVES AS ANTI-INFLUENZA AGENTS

[75] Inventors: Kuo-Hom L. Hsu, Fort Washington, Pa.; Daniel M. Teller, Columbus, Ohio; Alan R. Davis, Wayne; Michael D. Lubeck, Glenmoore, both of Pa.; Harry R. Munson, Jr., Loveland, Ohio; Gunnar E. Jagdmann, Apex, N.C.; Ibrahim M. Uwaydah, Richmond, Va.

[73] Assignee: American Home Products Corporation, Madison, N.J.

[21] Appl. No.: 47,730

[22] Filed: Apr. 15, 1993

[51] Int. Cl.⁶ ............... C07d 213/57; A61K 31/44
[52] U.S. Cl. .................... 514/357; 546/283; 546/330
[58] Field of Search ............... 546/330, 283; 514/357

[56] References Cited

U.S. PATENT DOCUMENTS 4,806,553 2/1989 Shiokawa .................. 514/332

FOREIGN PATENT DOCUMENTS 282904A 9/1988 European Pat. Off. ........ 544/124
417751A 6/1990 European Pat. Off. ........ 546/280
53-108970 9/1978 Japan ........................... 546/330

Primary Examiner—Alan L. Rotman
Attorney, Agent, or Firm—Robert F. Boswell, Jr.

[57] ABSTRACT

Antiinfluenza A activity was found in compounds of the formula:

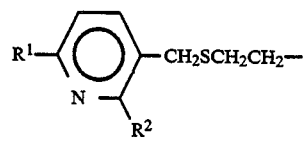

wherein: X is 2-phenylethyl, 2-furanylmethyl, or

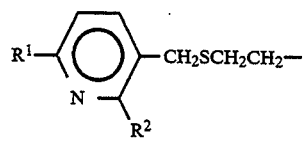

where one of $R^1$ and $R^2$ is H and the other is phenylamino;

Z is —$SCH_3$ when X is

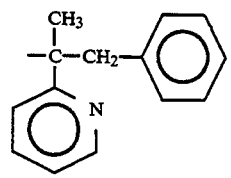

or when X is 2-phenylethyl or 2-furanylmethyl; or a pharmaceutically acceptable salt thereof.

5 Claims, No Drawings

N-CYANOAMIDINE DERIVATIVES AS ANTI-INFLUENZA AGENTS

FIELD OF INVENTION

This invention relates to antiviral activity of several novel cyanoimino compounds. Belshe and Hay, J. Respiratory Diseases 10:552-561, 1989, hypothesize that the M2 protein of influenza virus and the SH protein of respiratory syncytial viruses may function as ion channels. Several compound possessing the N-cyanoamidine moiety, analogs of a known potassium channel opener, pinacidil (N-cyano-N'-4-pyridinyl-N''-1,2,2-trimethylpropylguanidine), were tested and found to have antiviral activity against influenza A virus but were inactive against respiratory syncytial virus.

DESCRIPTION OF THE INVENTION

The novel compounds useful in this invention are represented by Formula I below:

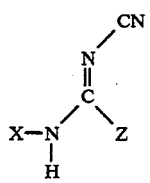

Formula I wherein: X is 2-phenylethyl, 2-furanylmethyl, or

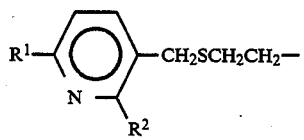

where one of $R^1$ and $R^2$ is H and the other is phenylamino;

Z is —SCH₃ when X is

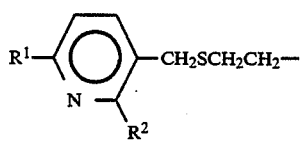

or

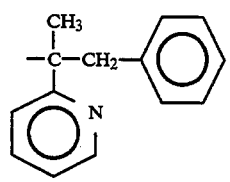

when X is 2-phenylethyl or 2-furanylmethyl; and the pharmaceutically acceptable salts thereof.

The term "pharmaceutically acceptable salts" encompasses hydrates, solvates, and acid addition salts formed from a basic compound of Formula I and a pharmaceutically acceptable inorganic or organic acid including but not limited to hydrochloric, hydrobromic, sulfuric, phosphoric, acetic, fumaric, succinic, maleic, tartaric, citric and ethanesulfonic acids.

The Formula I compounds where Z is a 2-methyl-2-(2-pyridinyl)phenylethyl are prepared by reacting an isothiocyanate of the formula X—N=C=S where X is 2-furanylmethyl or 2-phenylethyl with the lithio derivative of 1-phenyl-2-(2-pyridinyl)propane (α-methyl-β-phenyl-2-pyridineethane) followed by reaction with methyl iodide and then reacting the intermediate iminothioic acid methyl ester thus formed with cyanamide as shown in Scheme I below.

Scheme I.

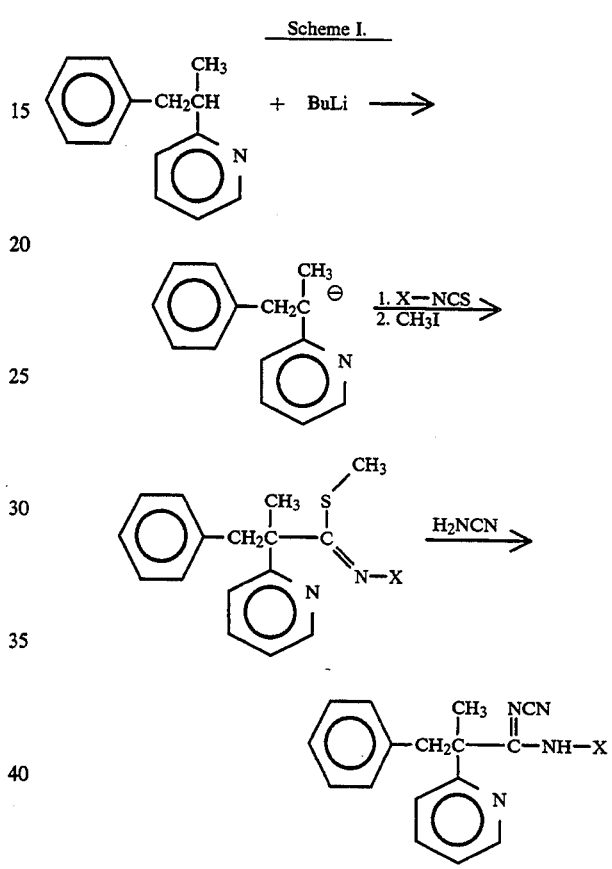

The Formula I compounds where Z is —SCH₃ are prepared by reacting an amine of the formula X—NH₂ where X is

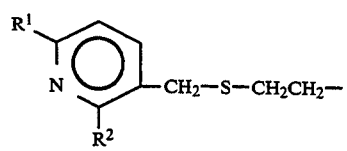

with dimethyl(cyanoimido)dithiocarbonate as shown in Scheme II. Scheme II.

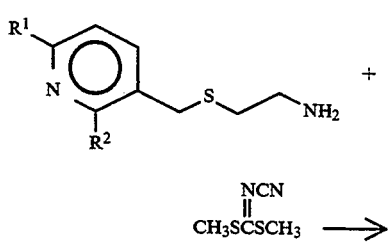

-continued

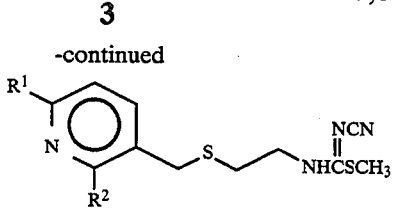

The amine of the formula X—NH$_2$ used in Scheme II is prepared by reacting 2-(or 6)-anilinopyridine-3-methanol with 2-aminoethanethiol hydrochloride in 48% hydrobromic acid.

The following synthetic procedures are included for illustrative purposes only and are not intended to be limiting in any way to this disclosure which is limited only by the scope of the appended claims.

EXAMPLE 1

N'-Cyano-α-methyl-N-(2-phenylethyl)-α-(phenylmethyl)-2-pyridineethanimidamide (A) α-Methyl-β-phenyl-2-pyridineethane A solution of 2-ethylpyridine (6.43 g, 60 mmol) dissolved in 100 mL of anhydrous tetrahydrofuran under nitrogen was cooled to −35° C., and treated (via syringe) with 2.20N n-butyllithium/hexane (27.3 mL, 60 mmol). The solution was stirred at −20 (±5)° C. for 25 minutes, treated at −40° C. (via syringe) with benzyl bromide (10.26 g, 7.14 mL, 60 mmol), warmed to 25° C., and stirred for 30 minutes. The solution was plunged into a stirred mixture of 300 mL of chloroform and 150 mL of ice water, and the organic layer was separated. The aqueous layer was extracted with 100 mL of chloroform and the combined organic extracts were washed with 150 mL of brine, dried (Na$_2$SO$_4$), and concentrated in vacuo to afford the intermediate used in the following reaction without further purification.

(B) α-Methyl-N-(2-phenylethyl)-α-(phenylmethyl)-2-pyridineethaniimidothioic acid, methyl ester A solution of α-methyl-β-phenyl-2-pyridineethane (5.13 g, 26 mmol) in 50 mL of anhydrous tetrahydrofuran at −35° C. under nitrogen was treated (via syringe) with 25 mmol (11.14 mL) of 2.20N n-butyllithium/hexane and stirred at −25 (±5)° C. for 30 minutes. The solution was transferred by a cannula over a 20 minute period into a solution of 2-phenylethyl isothiocyanate (4.41 g, 27 mmol) in 25 mL of anhydrous tetrahydrofuran at −70° C. under nitrogen. The mixture was warmed to 25° C. over 1 hour, stirred 30 minutes, cooled (0° C.), treated (via syringe) with methyl iodide (3.97 g, 1.75 mL, 28 mmol), and stirred at 25° C. for an additional 30 minutes. The cooled (0° C.) solution was poured into a stirred mixture of 300 mL of chloroform and 150 mL of ice water, and the organic layer was separated. The aqueous layer was extracted with 100 mL of chloroform and the combined organic extracts were washed with 150 mL of brine, dried (Na$_2$SO$_4$), and concentrated in vacuo to afford the crude intermediate which was used without further purification.

(C) Title compound

The above material was dissolved in 30 mL of methylene chloride and treated with cyanamide (1.26 g, 30 mmol) in 12 mL of ether. Additional 700 mg portions of cyanamide in ether were added after 18 hours and after 26 hours. After a total of 40 hours, the solution was filtered through alumina (eluted with 10% acetone/chloroform), concentrated in vacuo, and triturated from cold ether. Recrystallization from ethyl acetate/hexane afforded 5.07 g (55.0%) of the title compound as a white solid; mp 162.5°–163.5° C.

Analysis: Calculated for C$_{22}$H$_{20}$N$_4$: C, 78.23; H, 6.56: N, 15.20 Found: C, 78.01; H, 6.53: N, 15.10

EXAMPLE 2

N'-Cyano-N-(2-furanylmethyl)-α-methyl-α-(phenylmethyl)-2-pyridineethanimidamide (A) N-(2-Furanylmethyl)-α-methyl-α-(phenylmethyl)-2-pyridineethanimidothioic acid, methyl ester A solution of 2-(1-methyl-2-phenylethyl)pyridine (6.12 g, 31 mmol) in 60 mL of anhydrous tetrahydrofuran under nitrogen at −35° C. was treated (via syringe) with 2.50 N n-butyllithium/hexane (30 mmol), and stirred at −25(±5)° C. for 30 minutes. The mixture was transferred via a cannula over a 15-minute period into a cooled (−70° C.) solution of 2-furanylmethyl isothiocyanate (prepared in 89% yield from 2-furanylmethylamine by the procedure of J. C. Jochims and A. Seeliger, Angew. Chem. Int. Ed. Engl. 6, 174–175 (1967) (4.45 g, 32 mmol) in 25 mL of anhydrous tetrahydrofuran under nitrogen. The solution was warmed to 25° C. over one hour, maintained at room temperature for 30 minutes, cooled (0° C.), and treated (via syringe) with methyl iodide (4.68 g, 2.05 mL, 33 mmol). After 30 minutes at room temperature, the cooled (0° C.) solution was poured into a stirred mixture of 300 mL of chloroform and 150 mL of ice water. The organic layer was separated, and the aqueous solution was extracted with 150 mL of chloroform. The combined organic extracts were washed with 150 mL of brine, dried (Na$_2$SO$_4$) and concentrated in vacuo to afford the crude intermediate used below without further purification.

(B) Title compound

The crude intermediate was dissolved in 30 mL of methylene chloride and treated with cyanamide (1.68 g, 40 mmol) in 15 mL of ether. After 18 hours, an additional 800 mg of cyanamide was added in ether, and after 72 hours the solution was filtered through alumina (eluted with 10% acetone/chloroform) and chromatographed on silica gel (chloroform, then 5% acetone/chloroform as eluents). The product was triturated from cold ether and recrystallized from 2-propanol to afford 2.51 g (14%) of the title compound as a white solid; mp 152.5°–153.5° C.

Analysis: Calculated for C$_{21}$H$_{20}$N$_4$O: C, 73.24; H, 5.85; N, 16.27 Found: C, 73.56; H, 5.91; N, 16.27

EXAMPLE 3

N'-cyano-N-[2-[[[2-(phenylamino)-3-pyridinyl]methyl]thio]ethyl]carbamimidothioic acid methyl ester (A) 2-(Phenylamino)-3-pyridinecarboxylic acid To a suspension of 31.5 g (0.2 mole) of 2-chloro-3-pyridinecarboxylic acid in 75 mL of xylene was added 18.6 g (0.2 mole) of aniline, and the reaction mixture was heated at 190° C. (oil bath) for 45 min; then cooled. The xylene was filtered, and the reaction melt that had formed was crushed and partitioned between 100 mL of aqueous NaHCO$_3$ (pH 8) and CH$_2$Cl$_2$ (150 mL). The solid that remained suspended in the two-phase system was filtered and discarded. The filtrate was concentrated to 200 mL, and the solid that precipitated from the two-phase system was filtered to give 7.6 g (13%) of N-phenyl-2-(phenylamino)-3-pyridinecarboxamide.

Acetic acid was added to the filtrate to acidify the aqueous layer to pH 6 and the CH$_2$Cl$_2$ layer was separated. The aqueous solution was extracted with CH$_2$Cl$_2$ and the combined extracts were concentrated to 100 mL; the solid that precipitated was filtered and washed sequentially with water and $CH_2Cl_2$ to give 15.6 g of the product. An additional 5.3 g of the product was obtained from the filtrate for a total yield of 20.9 g (49%). The combined product was triturated with $CH_2Cl_2$ and then filtered to give 19.6 (46%) of the product as a yellow solid; mp 152°-155° C.; TLC ($C_6H_{12}$-EtAc; 4:1 and EtAc-MeOH-$NH_4OH$, 16:3:1) showed a single component. MS (EI) m/e (relative intensity): 214 (M+, 100), 213 (94), 195 (70), 169 (45), 168 (70), 167 (22), 77 (37), 51 (26).

Analysis: Calculated for $C_{12}H_{10}N_2O_2$: C, 67.28; H, 4.71; N, 13.08 Found: C, 67.15; H, 4.67; N, 13.07

(B) 2-(Phenylamino)-3-pyridinemethanol

To a refluxing solution of 6.5 g (30.4 mmole) of 2-phenylamino-3-pyridinecarboxylic acid and 7.5 mL (64.2 mmoles) of trimethylborate in 40 mL of THF under $N_2$ was added dropwise, 65 mL (130 mmole) of 2M borane-methyl sulfide over a 30 min period. The reaction mixture was refluxed for 2 hrs, then cooled, and 50 mL of $CH_3OH$ was added dropwise with stirring over a period of 30 min. The mixture was refluxed for 5 min, and the solvents were evaporated to leave a gummy light yellow semi-solid which was partitioned between 250 mL of 2N HCl and 150 mL of $CH_2Cl_2$. The aqueous layer was separated and brought to pH 8 ($NaHCO_3$), and the mixture was extracted with $CH_2Cl_2$ (700 mL). The $CH_2Cl_2$ was evaporated to leave 3.0 g of semi-solid which was purified by dry-column chromatography (glass column, 4×60 cm; 235 gm of silica; eluted with $CH_2Cl_2$). The fractions containing the product were extracted with $CH_2Cl_2$ then with $CH_3OH$. The solvents were evaporated, and the oily residue was converted to the HCl salt in acetone-$Et_2O$ to give 1.4 g (40%) of creamcolored solid; mp 180°-182° C. (J. Med. Chem. 11, 894 (1968), mp 189°-190° C.). MS (EI) m/e (relative intensity): 200 (M+, 27), 199 (24), 182 (65), 181 (100).

Analysis: Calculated for $C_{12}H_{13}ClN_2O$: C, 60.89; H, 5.54; N, 11.84 Found: C, 60.48; H, 5.57; N, 11.77

(C) 2-[[[2-(phenylamino)-3-pyridinyl]methyl]thio]ethylamine

A solution containing 8.0 g (40.0 mole) of 2-(phenylamino)-3-pyridinemethanol and 5.0 g (44.0 mmole) of 2-aminoethanethiol hydrochloride in 80 n4, of 48% HBr was refluxed for 25 hrs, then cooled. The solvent was evaporated in vacuo to leave a residue which was stirred with 100 mL of $H_2O$, and the insoluble solid that remained was filtered, washed ($H_2O$, then with petroleum ether, 30°-60° C.) and air-dried to give 11.3 g (67%) of the dihydrobromide salt; mp 187°-292° C. An additional 2.2 g of the product (as the free base) was obtained from the filtrate upon treatment with $K_2CO_3$ (pH 10) and extraction with $CH_2Cl_2$; total yield (81%).

(D) Title Compound

A solution containing 6.5 g (0.025 mole) of 2-[[[2-(phenylamino)-3-pyridinyl]methyl]thio]ethylamine, 3.7 g (0.025 mole) of dimethyl(cyanoimido)dithiocarbonate and 3 ml (0.022 mole) of $Et_3N$ in 50 mL of $CH_3CN$ was stirred at room temperature for 18 hrs, then refluxed for 3 hrs. The progress of the reaction was followed by TLC ($CH_2Cl_2$-MeOH, 10:1). The solvent was evaporated and the dark oily residue was purified by chromatography (3.5×70 cm glass column; 240 g of silica, eluted with $CH_2Cl_2$-EtAc, (1:1). Fractions containing the product were evaporated to give 6.1 g (68%); a 3.5 g sample was triturated with $CH_2Cl_2$, the solid was filtered to give 2.7 g (30%) of white solid; mp 120°-123° C. MS (EI)m/e (relative intensity): 357 (M+, 7), 309 (14), 308 (13), 215 (45), 184 (42), 183 (98), 182 (85), 181 (100), 77 (23), 48 (44), 47 (56), 45 (32).

Analysis: Calculated for $C_{17}H_{19}N_5S_2$: C, 57.12; H, 5.36; N, 19.59 Found: C, 56.92; H, 5.37; N, 19.51

EXAMPLE 4

N'-cyano-N-[2-[[[2-(phenylamino)-5-pyridinyl]methyl]-thio]ethyl]carbamimidothioic acid methyl ester (A) 6-Phenylamino-3-pyridinecarboxylic acid 6-Chloro-3-pyridinecarboxylic acid (15.76 g, 0.1 mole) and aniline (9.3 g, 0.1 mole) were heated together in 50 mL xylene at 180°-185° C. (oil bath) for 3 hours. After cooling, the solid that formed was filtered and washed with $Et_2O$. The solid was triturated with $NaHCO_3$ solution (pH 8), then filtered to give 7.0 g (24%) of N-phenyl-6-(phenylamino)-3-pyridinecarboxamide.

The aqueous $NaHCO_3$ solution was carefully neutralized with glacial HOAc (pH 6), and the solid that precipitated was filtered and washed. ($H_2O$ and with $Et_2O$); yield 12.13 g (57%), mp 264°-266° C. MS (EI) m/e 214 (M+), 213 (M-1, base), 169 (M-45), 167 (M-47).

Analysis: Calculated for $C_{12}H_{10}N_2O_2$: C, 67.28; H, 4.71; N, 13.08 Found: C, 67.03; H, 4.64; N, 13.01

(B) 6-Phenylamino-3-pyridinemethanol

Following the procedure given in part B of Example 3, 6-phenylamino-3-pyridinemethanol was prepared in 78% yield from 6-phenylamino-3-pyridinecarboxylic acid.; mp 119°-122° C.

(C) 2-[[[6-(phenylamino)-3-pyridinyl]methyl]thio]ethylamine

Following the procedure given in part C of Example 3, the title compound was prepared from 6-phenylamino-3-pyridinemethanol and 2-aminoethanethiol hydrochloride.

(D) Title compound

A solution containing 4.0 g (15.4 mmole) of 2-[[[6-(phenylamino)-3-pyridinyl]methyl]thio]ethylamine, 2.3 g (15.7 mmole) of dimethyl(cyanoimido)dithiocarbonate and 1.7 g (16.8 mmole) of $Et_3N$ dissolved in 60 ml of MeCN was stirred at room temperature for 15 minutes during which time a yellow precipitate formed. TLC ($CH_2Cl_2$-MeOH, 10:1) showed that the reaction was complete. The product was filtered to give 4.5 g (82%) of a yellow solid, mp 180°-182° C., MS m/e (relative intensity): (CI) 358 (M+1, 8), 183 (22), 128 (100): (EI) 309 (23), 183 (100), 182 (52), 77 (34), 48 (36), 47 (58).

Analysis: Calculated for $C_{17}H_{19}N_5S_2$: C, 57.12; H, 5.36; N, 19.59 Found: C, 57.42; H, 5.40; N, 19.80

The anti-influenza A activities were determined in Madin Darby Canine Kidney (MDCK) cells seeded in 96-well tissue culture plates. The test compounds (0.16-16 μg/ml) were added to the cells 2 hours prior to infecting the MDCK cells with FluA/WSN (~25 plaque forming units (PFU)/well). The plates were stained with crystal violet 2 days later to reveal the cytopathic effects. Antiviral activities were determined in triplicate while cellular toxicities were determined in a single test. Tests on the known antiviral agents amantadine and ribavirin were run for comparative purposes. Activity against respiratory syncytial virus (RSV) was determined similarly in HEp-2 cells except that ~500 PFU/well of RSV$A_2$ were added and the plates were stained 3 days after infection. Cytotoxicity in five different cell lines was determined. The results of these assays are shown in Table 1.

TABLE 1

Antiviral and Cytotoxicity Data

| Compound | Antiviral MI C$_{50}$ (μg/ml) | | Cytoxicity (minimal toxic dose μg/ml) | | | | |
|---|---|---|---|---|---|---|---|
| | A/WSN | RSVA$_2$ | MDCK | HEp-2 | A549 | MRC-5 | Vero |
| Example 1 | 0.16–0.5 | — | >50 | >50 | >50 | >50 | >50 |
| Example 2 | 0.16–0.5 | — | >50 | >50 | >50 | >50 | >50 |
| Example 3 | 0.5 | — | >100 | >100 | >100 | >100 | >100 |
| Example 4 | 5 | — | | | | | |
| Amantadine | 16 | — | >100 | >100 | >100 | >100 | >100 |
| Ribavirin | 1.6–5.0 | 1.6–5.0 | >100 | >100 | >100 | >100 | >100 |

Strain specificity of the antiinfluenza activities of the compounds of Examples 1 and 2 against two additional strains of influenza A and one strain of influenza B were determined. Both compounds were active against A/WSN and A/Kaw but were inactive against A/LA and B/Yama. The known antiviral compounds amantadine and ribavirin showed different specificities. Results of the strain specificity assays are shown in Table II.

TABLE II

Antiinfluenza Strain Specificity

| Virus[a] | Median Inhibiting Concentration (IC$_{50}$ μg/ml) | | | |
|---|---|---|---|---|
| | Example 1 | Example 2 | Amantadine | Ribavirin |
| FluA/WSN | 0.16–0.5 | 0.16–0.5 | 16 | 1.6–5 |
| FluA/Kaw | 0.5–1.6 | 0.5–1.6 | 0.5–1.6 | >16 |
| FluA/LA | >16 | >16 | 0.16 | >16 |
| FluB/Yama | >16 | >16 | >16 | 1.6–5 |

[a]A/WSN was tested in MDCK cells; A/Kaw, A/LLA and B/Yama were tested in chick kidney primary cultures.

Based on the in vitro antiinfluenza A test data of the invention compounds as compared with amantadine, which has a recommended daily dose of 200 mg in a normal human adult under age 65 for the treatment of influenza A, the dosage of a compound of this invention would be in the range of 2 to 200 mg/day which may be given in one dose or divided doses. The exact dosage will, of course, be determined according to standard medical principles by a physician.

The compounds may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredients. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carder can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

For administration by intranasal or intrabronchial inhalation or insufflation, compounds of this invention can be formulated into an aqueous or partly aqueous solution, which can then be utilized in the form of an aerosol.

Liquid pharmaceutical compositions which are sterile solutions or suspensions can be utilized by, for example, intramuscular, intraperitoneal or subcutaneous injection. Sterile solutions can also be administrated intravenously. The compound can also be administered orally either in liquid or solid composition form.

What is claimed is:

1. A compound of the formula:

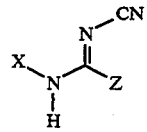

wherein:

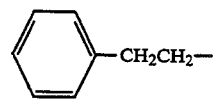

and Z is

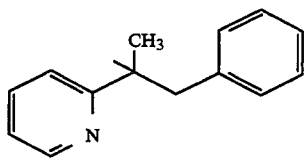

or a pharmaceutically acceptable salt thereof.

2. A compound according to claim 1 which is N'-cyano-α-methyl-N-2-(phenylethyl)-α-(phenylmethyl)-2-pyridinethanimidamide or a pharmaceutically acceptable salt thereof.

3. A method of treating influenza A infections in mammals which comprises administration to the mammal in need thereof a therapeutically effective amount of a compound of the formula:

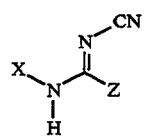

wherein X is

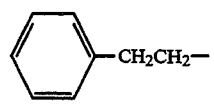

and Z is

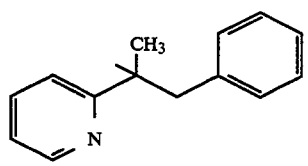

or a pharmaceutically acceptable salt thereof.

4. A method of treatment according to claim 3 wherein the compound used is N'-cyano-α-methyl-N-2-(phenylethyl)-α-(phenylmethyl)-2-pyridinethanimidamide or a pharmaceutically acceptable salt thereof.

5. A pharmaceutical composition for treating influenza A infection in mammals comprising a pharmaceutically acceptable carrier and a therapeutically effective amount of a compound of the formula:

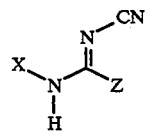

wherein: X is

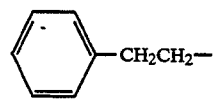

and Z is

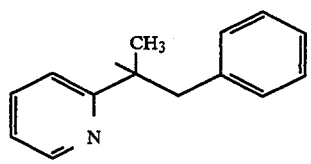

or a pharmaceutically acceptable salt thereof.

* * * * *